United States Patent
Seo et al.

(10) Patent No.: US 11,998,644 B2
(45) Date of Patent: Jun. 4, 2024

(54) DRY PAD

(71) Applicant: AMOLIFESCIENCE CO., LTD., Seoul (KR)

(72) Inventors: In Yong Seo, Seoul (KR); Ji Hyun Lee, Incheon (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 288 days.

(21) Appl. No.: 15/768,300

(22) PCT Filed: Oct. 17, 2016

(86) PCT No.: PCT/KR2016/011615
§ 371 (c)(1),
(2) Date: Apr. 13, 2018

(87) PCT Pub. No.: WO2017/065588
PCT Pub. Date: Apr. 20, 2017

(65) Prior Publication Data
US 2018/0303763 A1    Oct. 25, 2018

(30) Foreign Application Priority Data
Oct. 16, 2015    (KR) .......... 10-2015-0144640

(51) Int. Cl.
| | | |
|---|---|---|
| A61K 9/70 | (2006.01) | |
| A61F 13/00 | (2006.01) | |
| A61F 13/01 | (2024.01) | |
| A61K 33/38 | (2006.01) | |
| A61K 38/43 | (2006.01) | |
| A61K 45/06 | (2006.01) | |
| A61L 15/42 | (2006.01) | |
| A61L 15/44 | (2006.01) | |
| A61L 15/46 | (2006.01) | |
| A61L 15/60 | (2006.01) | |
| D04H 1/728 | (2012.01) | |
| A61K 47/64 | (2017.01) | |

(52) U.S. Cl.
CPC ............ *A61K 9/7007* (2013.01); *A61F 13/00* (2013.01); *A61F 13/00063* (2013.01); *A61F 13/01017* (2024.01); *A61F 13/01029* (2024.01); *A61K 33/38* (2013.01); *A61K 38/43* (2013.01); *A61K 45/06* (2013.01); *A61L 15/42* (2013.01); *A61L 15/44* (2013.01); *A61L 15/46* (2013.01); *A61L 15/60* (2013.01); *D04H 1/728* (2013.01); *A61K 47/64* (2017.08); *A61L 2300/104* (2013.01); *A61L 2300/254* (2013.01); *A61L 2300/404* (2013.01); *A61L 2300/414* (2013.01); *A61L 2300/428* (2013.01); *A61L 2400/12* (2013.01)

(58) Field of Classification Search
CPC ........ A61K 9/7007; A61F 13/00; D04H 1/728
See application file for complete search history.

(56) References Cited

U.S. PATENT DOCUMENTS

| | | | |
|---|---|---|---|
| 2006/0153904 A1* | 7/2006 | Smith | .............. D04H 1/728 424/448 |
| 2007/0286895 A1 | 12/2007 | Bowler et al. | |
| 2011/0111012 A1* | 5/2011 | Pepper | .............. A61F 13/00995 156/60 |
| 2014/0322512 A1* | 10/2014 | Pham | ................ D01D 5/0007 428/220 |
| 2018/0214597 A1* | 8/2018 | Gann | .................. A61L 15/46 |

FOREIGN PATENT DOCUMENTS

| | | |
|---|---|---|
| JP | 2000288018 | 10/2000 |
| KR | 20070051009 | 5/2007 |
| KR | 20100021108 | 2/2010 |
| KR | 101429455 | 8/2014 |
| WO | 03057267 | 7/2003 |

OTHER PUBLICATIONS

Liu, C. et al. "Using Carboxymethyl Cellulose as the Additive With Enzyme-Catalyzed Carboxylated Starch to Prepare the Film With Enhanced Mechanical and Hydrophobic Properties" Frontiers in Bioengineering and Biotechnology 2021, vol. 9, 1-11 (Year: 2021).*
International Search Report—PCT/KR2016/011615 dated Jan. 19, 2017.

* cited by examiner

*Primary Examiner* — Andrew S Rosenthal
(74) *Attorney, Agent, or Firm* — CANTOR COLBURN LLP

(57) ABSTRACT

Provided is a dry pad, including a wound-covering membrane formed by arranging a fiber containing a hydrophilic polymer that is swollen by an exudate secreted from a wound, a hydrophobic polymer, and a dry wound-healing agent that is released through swelling of the hydrophilic polymer and is difficult to store in a liquid phase, and a first release member, which is a support on which the fiber is arranged and which is separated from the wound-covering membrane.

14 Claims, 2 Drawing Sheets

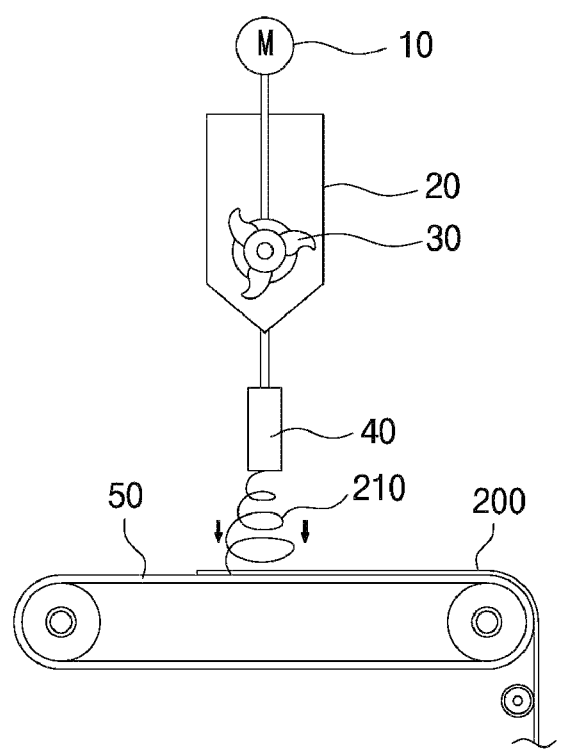

DRY PAD

TECHNICAL FIELD

The present invention relates to a dry pad, and more particularly to a dry pad, in which a wound-healing agent that is difficult to store in a liquid phase is contained in a dry fiber, thus enabling the long-term storage thereof and maximizing the wound-healing effect.

BACKGROUND ART

Typically, when a wound occurs, a wound-covering pad for treating the wound is used so as to sufficiently cover the surface of the wound depending on the amount of exudates generated from the wound after performing wound disinfection, and is then fixed in place with a piece of medical tape.

The wound-covering pad plays a role in protecting the wound, absorbing the exudate, promoting hemostasis, and supporting the wound, and the rate of healing is increased by covering the wound surface, which is a skin defect due to burns, wound, bedsores and trauma.

Korean Patent Application Publication No. 2010-0021108 discloses an antimicrobial dressing laminate, comprising a nanofiber member containing silver nanoparticles, an exudate-absorbing member formed on the nanofiber member, and a cover member as a semi-transparent film formed on the exudate-absorbing member, wherein the nanofiber member containing the silver nanoparticles is composed of a nanofiber manufactured in the form of a web having a fiber diameter of less than 1 μm by electrospinning a spinning solution comprising a fiber-forming polymer and a silver (Ag) metal salt.

As disclosed in Korean Patent Application Publication No. 2010-0021108, the wound dressing is formed of the fiber, but only antimicrobial characteristics and exudate-absorbing performance are exhibited, undesirably resulting in a low rate of wound healing.

Thus, it is necessary to develop wound-covering pads for providing an optimal healing environment and for introducing a new functional concept.

DISCLOSURE

Technical Problem

The present invention has been made keeping in mind the problems encountered in the related art, and is intended to provide a dry pad, which enables the long-term storage of a wound-healing agent that is difficult to store in a liquid phase for a long period of time.

In addition, the present invention is intended to provide a dry pad, in which a wound-healing agent may be released to the wound region through swelling of a hydrophilic polymer by an exudate secreted from the wound, thus increasing the wound-healing effect.

Technical Solution

Therefore, an embodiment of the present invention provides a dry pad, comprising: a wound-covering membrane formed by arranging a fiber containing a hydrophilic polymer that is swollen by an exudate secreted from a wound, a hydrophobic polymer, and a dry wound-healing agent that is released through swelling of the hydrophilic polymer; and a first release member, which is a support on which the fiber is arranged and which is separated from the wound-covering membrane.

The dry wound-healing agent may be any one selected from among a vitamin, an enzyme, a protein, and a peptide-vitamin C derivative.

The first release member may be disposed on the lower surface of the wound-covering membrane, and the dry pad of the present invention may further comprise a second release member formed on the upper surface of the wound-covering membrane.

The fiber may further contain at least one wound-healing agent selected from among an epidermal growth factor (EGF), a fibroblast growth factor (FGF), a protein for healing, and an antimicrobial material.

Furthermore, the antimicrobial material may be any one selected from among a silver nanomaterial, silver particles, and a natural antimicrobial material. Here, the silver nanomaterial may be any one selected from among silver nitrate ($AgNO_3$), silver sulfate ($Ag_2SO_4$), and silver chloride ($AgCl$).

The silver particles may have a size smaller than the diameter of the fiber.

Meanwhile, the hydrophilic polymer may include PU (polyurethane) or hydrogel.

Also, the first release member may be any one selected from among a release film, release paper, and a nonwoven fabric.

Moreover, the fiber may have a diameter of 0.2 to 1.5 μm.

The hydrophilic polymer and the hydrophobic polymer may be mixed at a weight ratio of 3:7 to 9:1, and the dry wound-healing agent may be used in an amount of 0.1 to 15 wt % based on the total weight of the polymer.

The dry wound-healing agent includes a vitamin, and the vitamin may be used in an amount of 5 to 10 wt % based on the total weight of the polymer.

The dry wound-healing agent may be linked to or contained in a hydrophilic polymer chain and is thus incorporated into the fiber, and when the hydrophilic polymer absorbs water of the exudate and swells, particles of the dry wound-healing agent may be released.

The wound-covering membrane may have a structure comprising at least two layers, among which the layer that is disposed adjacent to the wound may be configured such that the hydrophilic polymer is provided in a large amount so as to achieve rapid swelling by the exudate.

Advantageous Effects

According to the present invention, a wound-healing agent that is difficult to store in a liquid phase for a long period of time is incorporated in a dry state into a fiber, thus enabling the long-term storage of the wound-healing agent, such as a vitamin, an enzyme, a protein, or a peptide-vitamin C derivative, which decomposes in a liquid phase.

According to the present invention, when the hydrophilic polymer is swollen by an exudate secreted from the wound, the wound-healing agent can be released to the wound region to thus maximize the wound-healing effect.

According to the present invention, the antimicrobial material is gradually released upon swelling of the hydrophilic polymer by the exudate, whereby the amount of the antimicrobial material coming into contact with the wound decreases to thus relieve pain and improve antimicrobial characteristics on the wound region.

BRIEF DESCRIPTION OF DRAWINGS

FIG. 3 schematically shows an electrospinning device for manufacturing a wound-covering membrane according to the present invention.

MODE FOR INVENTION

Hereinafter, a detailed description will be given of embodiments of the present invention with reference to the accompanying drawings.

Figure 1:
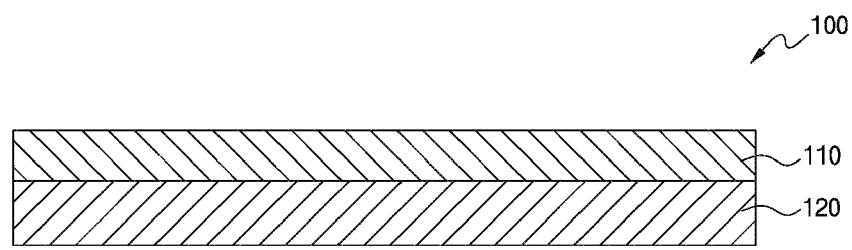
FIG. 1 is a cross-sectional view showing a dry pad having a two-layer structure according to the present invention.

As illustrated in FIG. 1, a dry pad 100 according to the present invention comprises a wound-covering membrane 110 formed by arranging a fiber 210 (FIG. 3) containing a hydrophilic polymer that is swollen by an exudate secreted from the wound, a hydrophobic polymer, and a dry wound-healing agent that is released through swelling of the hydrophilic polymer and is difficult to store in a liquid phase; and a release member 120, which is a support on which the fiber is arranged and which may be separated from the wound-covering membrane 110.

The dry pad 100 of the present invention may be utilized as any type of healing pad, such as a wound-covering pad or an atopy-healing pad, depending on the kind of dry wound-healing agent and the end use thereof.

Figure 2:
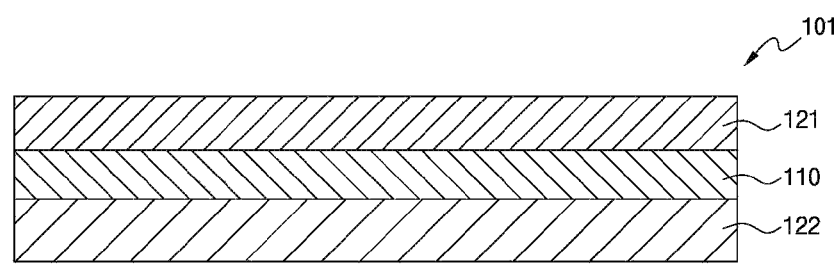
FIG. 2 is a cross-sectional view showing a dry pad having a three-layer structure according to the present invention.

In the present invention, a dry pad 100 having a two-layer structure comprising a wound-covering membrane 110 and a release member 120 may be manufactured, and, as illustrated in FIG. 2, a dry pad 101 having a three-layer structure comprising a first release member 121, a wound-covering membrane 110 and a second release member 122 may be provided.

Examples of the dry wound-healing agent may include a vitamin, an enzyme, a protein, and a peptide-vitamin C derivative, each of which decomposes in a liquid phase and is thus difficult to store in a liquid phase for a long period of time. In this case, the fiber containing the dry wound-healing agent may include a typical wound-healing agent.

In the present invention, the wound-healing agent that is difficult to store in a liquid phase is contained in a dry state in the fiber of the wound-covering membrane 110 of the dry pad 100, thereby enabling the long-term storage thereof in a dry state incorporated into the fiber. When the hydrophilic polymer is swollen by the exudate, the dry wound-healing agent may be released and transferred to the wound, thus realizing a quick wound-healing effect.

The hydrophilic polymer is a polymer that is characterized by swelling by absorbing a large amount of water from the exudate secreted from the wound, and may be exemplified by PU (polyurethane), hydrogel, etc.

In the dry pad of the present invention, the dry wound-healing agent is contained together with the hydrophilic polymer in the fiber. The dry wound-healing agent is provided in the form of particles having a size ranging from ones of nm to tens of nm to thus be linked to or contained in the hydrophilic polymer chain and thus become incorporated into the fiber. When the water of the exudate is absorbed into the hydrophilic polymer, the chain interval may increase and thus a swelling phenomenon may occur, whereby the dry wound-healing agent particles are released and the dry wound-healing agent is transferred to the wound, thus healing the wound.

Meanwhile, the peptide-vitamin C derivative is a peptide to which vitamin C is linked, and is specifically configured such that vitamin C is linked to a peptide, which is a polymer composed of 10 or fewer amino acids connected through peptide bonding.

The peptide-vitamin C derivative has a structure comprising a small number of bonded amino acids and thus facilitates penetration into the skin of the wound region.

Therefore, in the present invention, when the fiber of the wound-covering membrane 110 contains the wound-healing agent as well as the peptide-vitamin C derivative, the peptide-vitamin C derivative and the wound-healing agent contained in the fiber are released together upon swelling of the hydrophilic polymer by the exudate.

Here, the peptide-vitamin C derivative has a high ability to penetrate into the skin of the wound region to thus promote the penetration of the wound-healing agent into the wound, thus enabling quick wound recovery.

Also, in the present invention, the fiber of the wound-covering membrane 110 may further contain a wound-healing agent, such as a growth factor (GF) including an epidermal growth factor (EGF), a fibroblast growth factor (FGF), etc., a protein for healing, and an antimicrobial material.

The antimicrobial material is preferably any one selected from among a silver nanomaterial, silver particles, and a natural antimicrobial material such as chitosan. The silver nanomaterial may include a silver (Ag) metal salt, such as silver nitrate ($AgNO_3$), silver sulfate ($Ag_2SO_4$), and silver chloride (AgCl).

The antimicrobial material may be used in an amount of 1 to 10 wt % based on the total weight of the polymer. If the amount of the antimicrobial material is less than 1 wt % based on the total weight of the polymer, it is difficult to exhibit the desired performance due to the small amount thereof. On the other hand, if the amount thereof exceeds 10 wt %, the spinning solution cannot be electrospun, and even if the amount thereof is further increased, the antimicrobial activity is not further enhanced and costs may increase.

Furthermore, the silver particles may have a size smaller than the diameter of the fiber so that the silver particles are dispersed in the fiber.

In the dry pad 100 of the present invention, when the fiber of the wound-covering membrane 110 contains the antimicrobial material, the antimicrobial material is gradually released upon slow swelling of the hydrophilic polymer by the exudate, and thus a small amount of the antimicrobial material comes into contact with the wound, thereby relieving pain.

Specifically, in the case of a typical dry pad, which is coated with silver, silver is excessively released from the silver coating surface, and thus the patient may feel severe pain. Whereas, in the dry pad of the present invention, a small amount of antimicrobial material is gradually released and comes into contact with the wound, thus relieving the pain of the patient.

The wound-covering membrane 110 is formed by arranging the fiber, and thus may be configured to include a plurality of micropores formed between fibers.

The release member 110 may include a release film, release paper and a nonwoven fabric, formed of PET or PP.

Meanwhile, in the present invention, the wound-covering membrane 110 may be provided in a structure comprising at least two layers. Here, the diameter or pore size of the fiber of each layer may be designed to be different. When the layer is positioned closer to the wound, the hydrophilic polymer may be provided in a large amount so as to achieve rapid swelling by the exudate.

FIG. 3 schematically shows the electrospinning device for manufacturing the wound-covering membrane according to the present invention.

With reference to FIG. 3, the electrospinning device for manufacturing the wound-covering membrane according to the present invention is configured such that a stirring tank 20 for feeding a stirred spinning solution is connected to a spinning nozzle 40, a collector 50 grounded in the form of a conveyor moving at a predetermined rate is disposed at a lower position spaced apart from the spinning nozzle 40, and the spinning nozzle 40 is connected to a high-voltage generator.

Here, the hydrophilic polymer, the hydrophobic polymer, the dry wound-healing agent and the solvent are mixed using a stirrer 30 to give a spinning solution. Alternatively, a pre-mixed spinning solution may be used before being added to the electrospinning device, without the use of the stirrer 30.

Thereafter, when a high-voltage electrostatic force is applied between the collector 50 and the spinning nozzle 40, the spinning solution is made into an ultrafine fiber 210 using the spinning nozzle 40 and spun onto the collector 50, and the fiber 210 is arranged on the collector 50, thus forming a fiber web of the wound-covering membrane 200 for use in the dry pad.

More specifically, the spinning solution discharged from the spinning nozzle 40 is provided in the form of the fiber 210 while passing through the spinning nozzle 40 charged by the high-voltage generator, and the fiber 210 is sequentially stacked on the collector 50, which is grounded in the form of a conveyor moving at a predetermined rate, resulting in a fiber web for use in the wound-covering membrane 200.

The wound-covering membrane of the present invention is provided in the form of a fiber web having therein a plurality of pores obtained by electrospinning the spinning solution comprising the hydrophilic polymer, the hydrophobic polymer, the dry wound-healing agent and the solvent to give a fiber that is then arranged.

When the fiber of the fiber web contains all of the hydrophilic polymer, the hydrophobic polymer, and the dry wound-healing agent, the hydrophilic polymer and the hydrophobic polymer are mixed at a weight ratio of 3:7 to 9:1, and the dry wound-healing agent may be used in an amount of 0.1 to 15 wt % based on the total weight of the polymer. Furthermore, the vitamin is preferably used in an amount of 5 to 10 wt % based on the total weight of the polymer.

When the hydrophilic polymer and the hydrophobic polymer are mixed, if the amount of the water-soluble polymer is less than 30 wt %, hydrophilization does not occur upon swelling by the exudate. On the other hand, if the amount thereof exceeds 90 wt %, the web is not formed upon electrospinning the spinning solution in order to form the membrane 110 having the fiber web structure.

Also, if the amount of the dry wound-healing agent is less than 0.1 wt % based on the total weight of the polymer, it is difficult to exhibit the desired performance due to the small amount thereof. On the other hand, if the amount thereof exceeds 15 wt %, the spinning solution cannot be electrospun and costs may increase.

The wound-covering membrane used for the dry pad of the present invention includes the hydrophilic polymer in lieu of the water-soluble polymer because the polymer may be dissolved upon healing of the wound.

However, when polyurethane (PU) is used as the hydrophilic polymer, polyurethane (PU) has high elasticity, and thus, in order to suppress such elasticity, a polymer that has relatively low elasticity and is water-insoluble and hydrophobic is used, and examples thereof may include polyvinylidene fluoride (PVdF).

In the present invention, the fiber of the wound-covering membrane may have a diameter of 0.2 to 1.5 µm and a pore size of 0.2 to 1.5 µm. Also, the wound-covering membrane may have a thickness of 5 to 20 µm and a basis weight of 5 to 30 gsm.

If the thickness of the wound-covering membrane 110 is less than 5 µm and the basis weight thereof is less than 5 gsm, handling is difficult due to the low strength thereof. If the thickness of the wound-covering membrane 110 exceeds 20 µm and the basis weight thereof exceeds 30 gsm, transparency may be lost and costs may increase.

Meanwhile, the wound-covering membrane 110 is configured such that fibers of the fiber web have many micropores therein, and thus water contained in the exudate is absorbed into the micropores, whereby diffuse reflection does not occur and the membrane consequently appears transparent. When the water contained in the exudate is dried, the membrane turns to a white color or a color other than the white color, and may thus become opaque.

Accordingly, when the wound-covering membrane 110 is attached and fixed to the wound region, it changes from a transparent state to a semi-transparent or opaque state, from which the state of the wound region may be predicted without the need to open the attached wound-covering membrane 110, and thus the replacement time of the wound-covering membrane 110 may be predicted.

The hydrophobic polymer may be electrospun, and functions to maintain the structure of the wound-covering membrane 110, regardless of whether the hydrophilic polymer is swollen by the exudate and the wound-healing agent is released. As for the hydrophobic polymer, any resin may be used without particular limitation, so long as it is able to form a fiber through electrospinning, and a natural polymer may be used.

Examples of the useful hydrophobic polymer may include polyvinylene fluoride (PVdF), poly(vinylidene fluoride-co-hexafluoropropylene), perfluoropolymer, polyvinyl chloride, polyvinylidene chloride or copolymers thereof, polyethylene glycol derivatives including polyethylene glycol dialkyl ether and polyethylene glycol dialkyl ester, polyoxides including poly(oxymethylene-oligo-oxyethylene), polyethylene oxide and polypropylene oxide, polyvinyl acetate, poly(vinyl pyrrolidone-vinyl acetate), polystyrene and polystyrene acrylonitrile copolymers, polyacrylonitrile copolymers including polyacrylonitrile (PAN) and polyacrylonitrile methyl methacrylate copolymers, polymethyl methacrylate, polymethylmethacrylate copolymers, or mixtures thereof.

Also, examples of the usable hydrophobic polymer may include aromatic polyesters, such as polyamide, polyimide, polyamide imide, poly(meta-phenylene isophthalamide), polysulfone, polyether ketone, polyether imide, polyethylene terephthalate, polytrimethylene terephthalate, and polyethylene naphthalate, polyphosphagenes, such as polytetrafluoroethylene, polydiphenoxy phosphagene, and poly{bis[2-(2-methoxyethoxy)phosphagene]}, polyurethane copolymers (hydrophobic) including polyurethane and polyether urethane, cellulose acetate, cellulose acetate butylate, and cellulose acetate propionate.

The solvent may include at least one selected from the group consisting of DMAc (N,N-dimethylacetamide), DMF (N,N-dimethylformamide), NMP (N-methyl-2-pyrrolidinone), DMSO (dimethyl sulfoxide), THF (tetra-hydrofuran), EC (ethylene carbonate), DEC (diethyl carbonate), DMC (dimethyl carbonate), EMC (ethyl methyl carbonate), PC (propylene carbonate), water, acetic acid, formic acid, chloroform, dichloromethane, acetone, and isopropyl alcohol.

Although the preferred embodiments of the present invention have been disclosed for illustrative purposes, those skilled in the art will appreciate that various modifications and substitutions are possible, without departing from the scope and spirit of the invention as disclosed in the accompanying claims.

INDUSTRIAL APPLICABILITY

According to the present invention, a dry pad is configured such that a wound-healing agent that is difficult to store in a liquid phase is contained in a dry fiber, thus enabling the long-term storage thereof and maximizing the wound-healing effect.

The invention claimed is:

1. A dry pad, comprising:
a wound-covering membrane; and
a first release member on which the wound-covering membrane is disposed, wherein the first release member is configured to be able to be separated from the wound-covering membrane,
wherein the wound-covering membrane comprises: at least two layers of wound-covering membranes, the at least two layers of wound-covering membranes each being formed of electrospun fibers,
wherein each of the electrospun fibers is made of a solution consisting of a hydrophilic polymer, a hydrophobic polymer, and a dry wound-healing agent, wherein the hydrophilic polymer is configured to be swollen by an exudate secreted from a wound of a user, and the dry wound-healing agent is configured to be released towards the wound through swelling of the hydrophilic polymer, and
wherein, in the at least two layers of wound-covering membranes, a content of the hydrophilic polymer gradually increases towards the wound so as to achieve rapid swelling by the exudate.

2. The dry pad of claim 1, wherein the dry wound-healing agent is any one selected from the group consisting of a vitamin, an enzyme, a protein, and a peptide-vitamin C derivative.

3. The dry pad of claim 1, further comprising: a second release member, wherein the first release member is disposed on a surface of the wound-covering membrane, and the second release member is formed on the other surface of the wound-covering membrane.

4. The dry pad of claim 1, wherein the wound-healing agent contains at least one selected from the group consisting of an epidermal growth factor, a fibroblast growth factor, a protein for healing, and an antimicrobial material.

5. The dry pad of claim 4, wherein the antimicrobial material is any one selected from the group consisting of a silver nanomaterial, silver particles, and a natural antimicrobial material.

6. The dry pad of claim 5, wherein the silver nanomaterial is any one selected from the group consisting of silver nitrate ($AgNO_3$), silver sulfate ($Ag_2SO_4$), and silver chloride ($AgCl$).

7. The dry pad of claim 5, wherein the silver particles have a size smaller than a diameter of the electrospun fibers.

8. The dry pad of claim 1, wherein the hydrophilic polymer includes any one selected from the group consisting of PU (polyurethane) and hydrogel.

9. The dry pad of claim 1, wherein the first release member is any one selected from the group consisting of a release film, release paper, and a nonwoven fabric.

10. The dry pad of claim 1, wherein the electrospun fibers have a diameter of 0.2 to 1.5 μm.

11. The dry pad of claim 1, wherein the hydrophilic polymer and the hydrophobic polymer are mixed at a weight ratio of 3:7 to 9:1.

12. The dry pad of claim 11, wherein the dry wound-healing agent is used in an amount of 0.1 to 15 wt % based on a total weight of the hydrophilic polymer and the hydrophobic polymer.

13. The dry pad of claim 12, wherein the dry wound-healing agent includes a vitamin, and
the vitamin is used in an amount of 5 to 10 wt % based on the total weight of the hydrophilic polymer and the hydrophobic polymer.

14. The dry pad of claim 1, wherein the dry wound-healing agent is linked to or contained in a hydrophilic polymer chain of the hydrophilic polymer and incorporated into the electrospun fibers, and when the hydrophilic polymer absorbs water of the exudate and swells, particles of the dry wound-healing agent are released.

* * * * *